(12) United States Patent
Cho et al.

(10) Patent No.: US 7,201,846 B2
(45) Date of Patent: Apr. 10, 2007

(54) MICRO-FLUIDIC ANTI-MICROBIAL FILTER

(75) Inventors: Steven T. Cho, Castroville, CA (US); Harlow B. Christianson, San Jose, CA (US)

(73) Assignee: Hospira, Inc., Lake Forest, IL (US)

( * ) Notice: Subject to any disclaimer, the term of this patent is extended or adjusted under 35 U.S.C. 154(b) by 171 days.

(21) Appl. No.: 10/763,549

(22) Filed: Jan. 23, 2004

(65) Prior Publication Data

US 2004/0154972 A1 Aug. 12, 2004

Related U.S. Application Data

(62) Division of application No. 10/074,962, filed on Feb. 13, 2002, now abandoned.

(51) Int. Cl.
*B31D 3/00* (2006.01)
*C23F 1/02* (2006.01)
*B01D 29/01* (2006.01)

(52) U.S. Cl. .......................... 210/321.84; 216/2; 216/56; 210/490; 210/498; 210/500.26

(58) Field of Classification Search .................... 216/56
See application file for complete search history.

(56) References Cited

U.S. PATENT DOCUMENTS

| 3,423,261 A | * | 1/1969 | Frantzen ........................ 216/56 |
| 5,618,762 A | | 4/1997 | Shirakawa et al. |
| 5,651,900 A | | 7/1997 | Keller et al. |
| 5,681,468 A | * | 10/1997 | Sawan et al. ............ 210/500.25 |
| 5,753,014 A | | 5/1998 | Van Rijn |
| 5,919,364 A | | 7/1999 | Lebouitz et al. |
| 5,948,255 A | | 9/1999 | Keller et al. |
| 6,471,876 B1 | | 10/2002 | Hansen et al. |
| 6,622,872 B1 | * | 9/2003 | Tai et al. ..................... 210/490 |

FOREIGN PATENT DOCUMENTS

| DE | 36 31 804 A | 3/1988 |
| WO | 95 17152 | 6/1995 |
| WO | 01 85341 | 11/2001 |
| WO | 02 18058 | 3/2002 |

* cited by examiner

*Primary Examiner*—Krishnan S. Menon
(74) *Attorney, Agent, or Firm*—Michael R. Crabb (57) ABSTRACT

An anti-microbial filter (105) for a micro-fluidic system (100) includes a silicon-based filter membrane (213) having holes (218) formed therein. The membrane (213) is formed on a substrate (211). One side of the filter membrane (213) has an anti-microbial coating (216) between the holes (218) on the filter membrane (213) and the other side can include filter supports formed from a silicon substrate. A method for making the anti-microbial filter (105) includes forming a filter membrane (213) on a substrate (211), forming holes (218) in the membrane (213) by providing a filter mask (215) and etching holes (218) through holes (222) in the mask (215). Then portions of the substrate (211) are removed from the filter membrane (213) using a masking and etching process to expose the holes (218). An anti-microbial coating is applied to the membrane (213) adjacent the holes (218).

9 Claims, 6 Drawing Sheets

MICRO-FLUIDIC ANTI-MICROBIAL FILTER

CROSS-REFERENCE TO RELATED APPLICATIONS

This application is a divisional of U.S. Ser. No. 10/074,962 filed Feb. 13, 2002, now abandoned.

FIELD OF THE INVENTION

The present invention generally relates to filters for purification of fluids. More particularly, the present invention relates to a micro-fluidic anti-microbial filter.

BACKGROUND OF THE INVENTION

MEMS technology integrates electrical components and mechanical components on a common silicon substrate by using micro-fabrication technology. Integrated circuit (IC) fabrication processes, such as photolithography processes and other microelectronic processes, form the electrical components. The IC fabrication processes typically use materials such as silicon, glass, and polymers. Micro-machining processes, compatible with the IC processes, selectively etch away areas of the IC or add new structural layers to the IC to form the mechanical components. The integration of silicon-based microelectronics with micro-machining technology permits complete electro-mechanical systems to be fabricated on a single chip. Such single chip systems integrate the computational ability of microelectronics with the mechanical sensing and control capabilities of micro-machining to provide smart devices.

One type of MEMS is a micro-fluidic system. Micro-fluidic systems include components such as channels, reservoirs, mixers, pumps, valves, chambers, cavities, reaction chambers, heaters, fluidic interconnects, diffusers, nozzles, and other micro-fluidic components. These micro-fluidic components typically have dimensions between a few micrometers and a few hundreds of micrometers. These small dimensions minimize the physical size, the power consumption, the response time and the waste of the micro-fluidic system. Such micro-fluidic systems may provide wearable miniature devices located either outside or inside a human body or an animal body.

Applications for micro-fluidic systems include genetic, chemical, biochemical, pharmaceutical, biomedical, chromatography, IC cooling, ink-jet printer head, medical, radiological, environmental, as well as any devices that require liquid or gas filled cavities for operation. Such application may involve processes related to analysis, synthesis and purification. The medical applications include diagnostic and patient management such as implanted drug dispensing systems. The environmental applications include detecting hazardous materials or conditions such as air or water pollutants, chemical agents, biological organisms or radiological conditions. The genetic applications include testing and/or analysis of DNA.

An anti-microbial filter is a device that filters out microorganisms in a fluidic system. Anti-microbial filters are typically used for fluid purification, such as in air, water and drug delivery systems. In drug delivery systems, anti-microbial filters are used to prevent microorganisms in a human or an animal body from reaching the fluid source of the drug delivery. Some anti-microbial filters are made with holes that are large enough to permit fluid to flow through the filter in one direction, but small enough to prevent the microorganisms from moving through the filter in the opposite direction. Anti-microbial filters may also have a coating, such as silver, disposed on the downstream side of the filter that prevents some microorganisms from adhering to the filter and kills other microorganisms that contact the coating. Some anti-microbial filters have a long, narrow, winding path, otherwise known as a torturous path, which permits fluid to flow in one direction through the path while inhibiting the flow of microorganisms in the opposite direction. Anti-microbial filters have been made on a macro scale. However, making anti-microbial filters on a micro scale presents special challenges, such as the construction of very small holes with precision while being cost effective, manufacturable and reliable.

Accordingly, it would be desirable to have an anti-microbial filter that is small enough to be used in a micro-fluidic system. The anti-microbial filter would be constructed using micro-machining processes to permit it to be integrated into a micro-fluidic system. The micro-machining process would be precise and cost effective. Thus, the anti-microbial filter would be easy to manufacture and of high quality.

SUMMARY OF THE INVENTION

According to one aspect of the present invention, an anti-microbial filter adapted for a micro-fluidic system includes a filter membrane formed of a silicon-based material having a plurality of holes formed therein.

According to another aspect of the present invention, a support structure is connected to and extends from a first side of the filter membrane.

According to another aspect of the present invention, an anti-microbial coating is disposed between the holes on the filter membrane.

According to another aspect of the present invention, the micro-fluidic system includes a fluid source adapted to contain fluid, a fluid sink fluidly connected to the fluid source and adapted to receive the fluid, and the anti-microbial filter fluidly connected to the fluid source and the fluid sink.

According to another aspect of the present invention, the micro-fluidic system further includes an upstream channel fluidly connecting the fluid source to the anti-microbial filter and a downstream channel fluidly connecting the fluid sink to the anti-microbial filter.

According to another aspect of the present invention, a method for making an anti-microbial filter includes the steps of providing a substrate, forming the filter membrane on the substrate, forming the plurality of holes in the filter membrane, and removing at least a portion of the substrate to expose the plurality of holes in the filter membrane.

According to another aspect of the present invention, the step of forming the filter membrane further includes the step of diffusing filter material into a predetermined depth of the substrate, wherein the predetermined depth of the diffusion of the filter material into the substrate corresponds to a predetermined thickness of the filter membrane.

According to another aspect of the present invention, the step of forming the filter membrane further includes the step of depositing the filter membrane on the substrate.

According to another aspect of the present invention, the step of forming the plurality of holes in the filter membrane further includes the steps of providing a filter mask, having a plurality of holes, over the filter membrane, and forming the plurality of holes in the filter membrane corresponding to the plurality of holes in the filter mask.

According to another aspect of the present invention, the step of providing the filter mask further comprises the steps of depositing a plurality of spacers on the filter material, wherein a part of the plurality of spacers contacts the filter material, depositing filter mask material partially around the spacers and on the filter material, wherein the part of the plurality of spacers that contacts the surface of the filter material prevents the filter mask material from coming between the part of the plurality of spacers and the filter material, and removing the plurality of spacers to form the plurality of holes in the filter mask, wherein each spacer that contacts the filter material corresponds to each hole in the filter mask.

According to another aspect of the present invention, the step of removing the plurality of spacers further comprises the step of dissolving the plurality of spacers.

According to another aspect of the present invention, the step of removing the plurality of spacers further includes the step of disintegrating the plurality of spacers.

According to another aspect of the present invention, the step of forming the plurality of holes in the filter membrane further comprises the step of etching the filter membrane through the holes in filter mask.

According to another aspect of the present invention, the step of removing at least a portion of the substrate further comprises the step of removing portions of the substrate from the filter membrane, wherein the remaining portions of the substrate that contact the filter membrane provide the support structure for the filter membrane.

According to another aspect of the present invention, the step of removing at least a portion of the substrate further comprises the step of removing the entire substrate from the filter membrane.

According to another aspect of the present invention, an anti-microbial coating is deposited between the holes on the filter membrane.

These and other aspects of the present invention are further described with reference to the following detailed description and the accompanying figures, wherein the same reference numbers are assigned to the same features or elements illustrated in different figures. Note that the figures may not be drawn to scale. Further, there may be other embodiments of the present invention explicitly or implicitly described in the specification that are not specifically illustrated in the figures and vise versa.

DETAILED DESCRIPTION OF THE PREFERRED EMBODIMENTS

Figure 1:
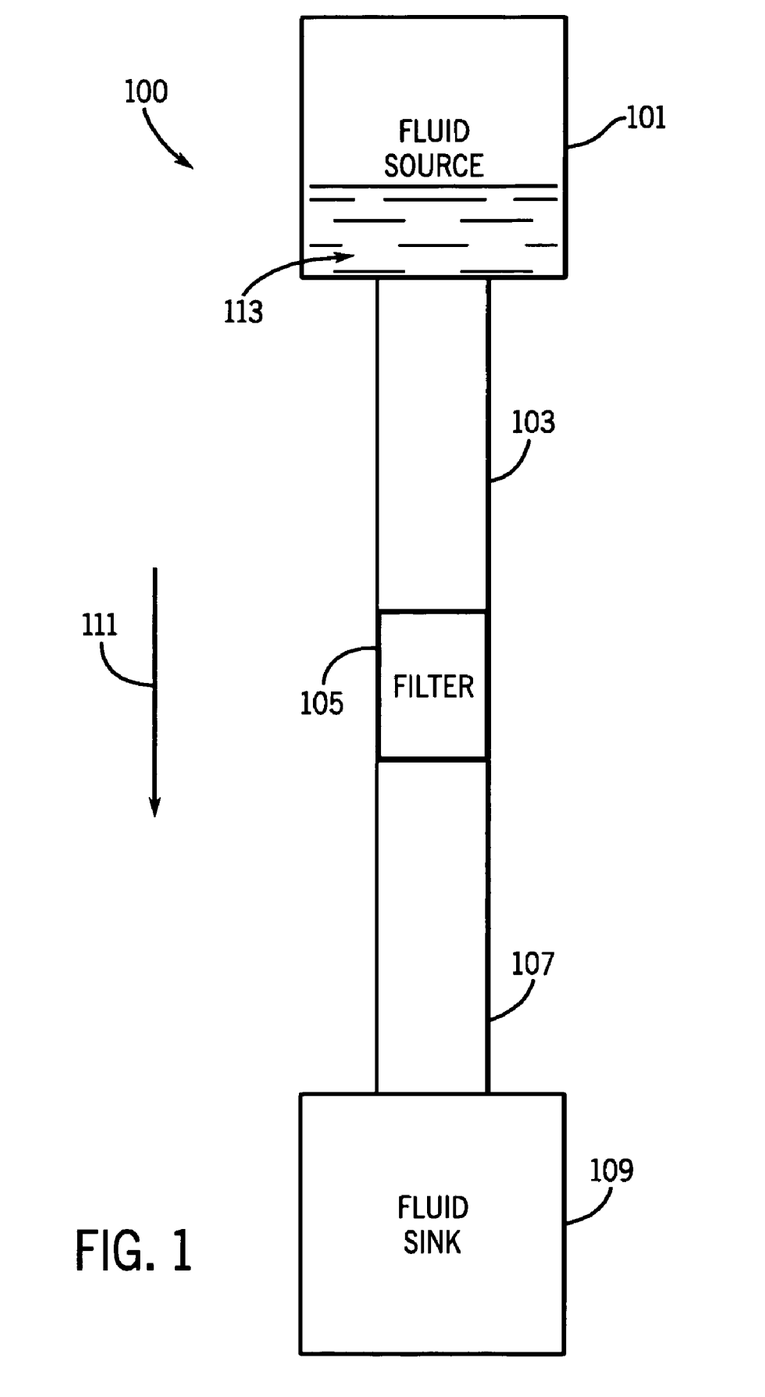
FIG. 1 illustrates a micro-fluidic system having an anti-microbial filter in accordance with a preferred embodiment of the present invention.

FIG. 1 illustrates a micro-fluidic system 100 having an anti-microbial filter 105 in accordance with a preferred embodiment of the present invention. The micro-fluidic system 100 is constructed using the MEMS technology described above. The micro-fluidic system 100 generally includes a fluid source 101, an upstream channel 103, the anti-microbial filter 105, a downstream channel 107, a fluid sink 109, and fluid 113. The fluid source 101 is fluidly connected to the fluid sink 109 through the upstream channel 103 and the downstream channel 107. The direction of fluid flow 111 in the micro-fluidic system 100 is from the fluid source 101 to the fluid sink 109. The anti-microbial filter 105 filters out microorganisms in the micro-fluidic system. In the preferred embodiment of the present invention, the anti-microbial filter 105 prevents microorganisms from moving from the downstream channel 107 or the fluid sink 109 to the upstream channel 103 or the fluid source 101. The anti-microbial filter 105 may filter fluid flowing between two micro-fluidic components. Preferably, the anti-microbial filter 105 filters fluid flowing between the upstream channel 103 and the downstream channel 107. Alternatively, the anti-microbial filter 105 may filter fluid flowing between the fluid source 101 and the upstream channel 103, or between the downstream channel 107 and the fluid sink 109, or between the fluid source 101 and the fluid sink 109 without the upstream channel 103 or the downstream channel 107.

The fluid source 101 contains the fluid 113 and represents any of the micro-fluidic components described above, including but not limited to reservoirs, mixers, and chambers. Similarly, the fluid sink 109 receives the fluid 113 and generically represents any of the micro-fluidic components described above.

The upstream channel 103 and the downstream channel 107 carry the fluid 113 between the fluid source 101 and the fluid sink 109. The upstream channel 103 and the downstream channel 107 may be formed as two separate channels connected by the anti-microbial filter 105 or as one integral channel having the anti-microbial filter 105 disposed therein. The fluid 113 flows from the fluid source 101 to the fluid sink 109 responsive to pressure exerted on the fluid 113. The pressure exerted on the fluid 113 may be supplied from an external source or an internal source relative to the micro-fluidic system 100. Examples of the external source of pressure include, without limitation, gravity and rotating mechanisms. An example of the internal source of pressure includes, without limitation, a pump. Preferably, the pump is also a component of the micro-fluidic system 100.

The fluid 113 may have any appropriate state that permits fluid flow, such as a liquid state or a gas state. The fluid 113 represents any composition of matter appropriate for applications of the micro-fluidic system 100, as described above. Examples of fluids 113 include, without limitation, chemical, bodily, hazardous, biological, and radiological fluids.

Biological fluids may be any biologically derived analytical sample, including, without limitation, blood, plasma, serum, lymph, saliva, tears, cerebrospinal fluid, urine, sweat, semen, and plant and vegetable extracts.

The micro-fluidic system 100 in FIG. 1 represents a relative simple system for the sake of clarity. In practice, the micro-fluidic system 100 may be a very complex system having many and/or duplicated micro-fluidic components, such as multiple anti-microbial filters 105. The micro-fluidic system 100, performing complex or parallel functions, typically needs many anti-microbial filters 105, such as greater than ten anti-microbial filters 105, to filter the fluids 113 moving throughout different parts of the micro-fluidic system 100 at the same time or different times. Therefore, it is desirable for the anti-microbial filters 105 to be compact, reliable, simple to fabricate, and easily integrated with the rest of the micro-fluidic system 100.

FIGS. 2A–2K illustrate, in a sequence of cross-sectional views, a micro-machined fabrication process for making the anti-microbial filter 105 of FIG. 1 in accordance with the preferred embodiment of the present invention. The FIGS. 2A–2K illustrate various materials being added or being removed to create the features of the anti-microbial filter 105. FIG. 3 illustrates a flowchart describing a method for making the anti-microbial filter 105 using the micro-machined fabrication process, as shown in FIGS. 2A–2K. The method includes a sequence of steps 302–312, inclusive. The steps 302–312 shown in FIG. 3 correspond to the cross-sectional views of FIGS. 2A–2K, respectively. Next, each of the steps in FIG. 3 and the corresponding cross-sectional view in FIGS. 2A–2K are described in detail.

Figure 2A:
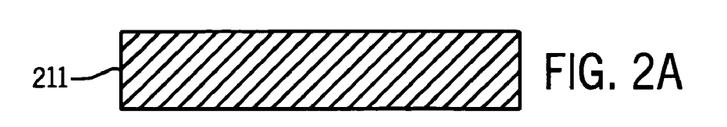
FIGS. 2A–K illustrate, in a sequence of cross-sectional views, a micro-machined fabrication process for making the anti-microbial filter of FIG. 1 according to the present invention.
Figure 3:
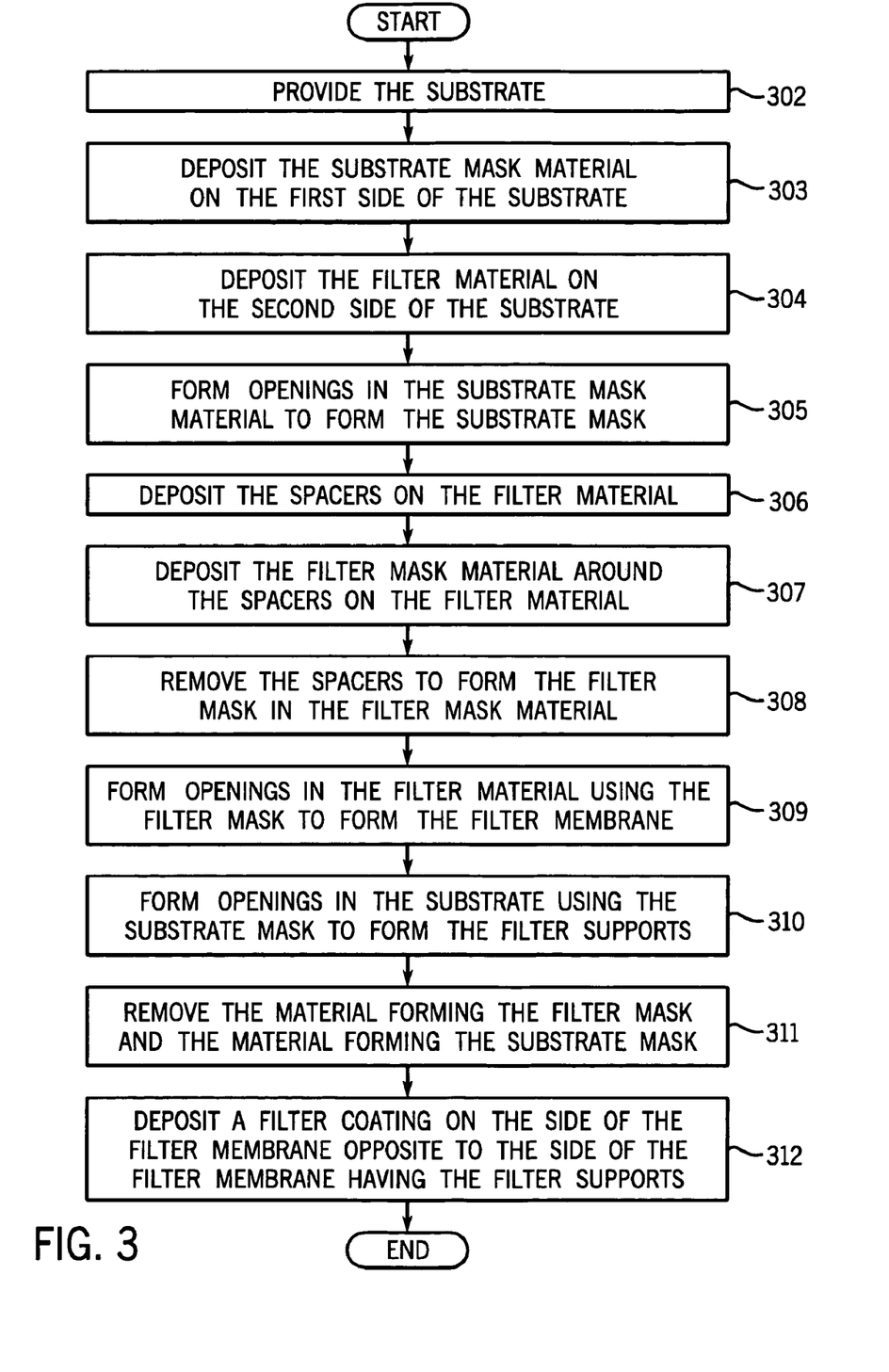
FIG. 3 illustrates a flowchart describing a method for making the anti-microbial filter using the micro-machined fabrication process of FIGS. 2A–2K.

At step 302 in FIG. 3, corresponding to FIG. 2A, a substrate 211 is provided. The substrate 211 may be formed of any material that is compatible with the micro machined fabrication process. Preferably, the substrate 211 is made of silicon. The substrate 211 is constructed using methods that are well known in the art of semiconductor manufacturing processing. The substrate 211 generally provides the foundation or platform on which to build the anti-microbial filter 105. The substrate 211 may have a thickness in the range of one to hundreds of microns, and is preferably 3 micrometers thick. In the preferred embodiment of the present invention, the substrate 211 also provides structural support for the anti-microbial filter 105, as a finished device, in the MEMS.

Figure 2B:
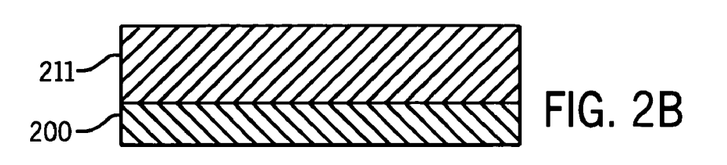

At step 303 in FIG. 3, corresponding to FIG. 2B, substrate mask material 200 is deposited on the first, preferably bottom, side of the substrate 211. The substrate mask material 200 may be formed of any material that is compatible with the micro machined fabrication process. Preferably, the substrate mask material 200 is silicon dioxide. Preferably, the substrate 202 and the substrate mask material 200 are provided together as a manufactured wafer. The substrate mask material 200 may be deposited on the substrate 211 using a variety of methods that are well known in the art of semiconductor manufacturing processing. The substrate mask material 200 may have a thickness in the range of hundreds to thousands of angstroms thick, and is preferably 1000 angstroms thick. The substrate mask material may be deposited on the substrate 211 using a variety of methods that are well known in the art of semiconductor manufacturing processes. The substrate mask material 200 is used later in the micro-machining process to form a substrate mask 212 for the substrate 211.

Figure 2C:
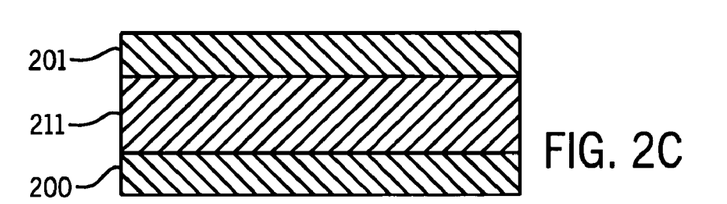

At step 304 in FIG. 3, corresponding to FIG. 2C, filter material 201 is formed on the second, top side of the substrate 211. The filter material 201 may be formed of any material that is compatible with the micro machined fabrication process. In the preferred embodiment, the filter material 201 is deposited on the substrate 211 using deposition processes such as electrochemical, ultrasonic spray, aerosol, or spin-on, that are well known in the art of semiconductor processing. Alternatively, the filter material 201 may be formed on the surface of the substrate 211 by doping the top surface of the substrate 211 with a silicon compatible material, such as boron. In this case, the thickness of the filter material corresponds to the depth of penetration of the filter material 201 into the surface of the substrate 211. When the filter material 201 is deposited, preferably, the filter material 201 is polysilicon, but may also be nitride, epitaxy, and the like. The filter material 201 may have a thickness in the range of 0.1–100 micrometers, and is preferably 3–5 micrometers thick. The filter material 201 is used later in the micro-machining process to form a filter membrane 213 for the anti-microbial filter 105, as a finished device, in the MEMS.

Figures 2D, 2E:
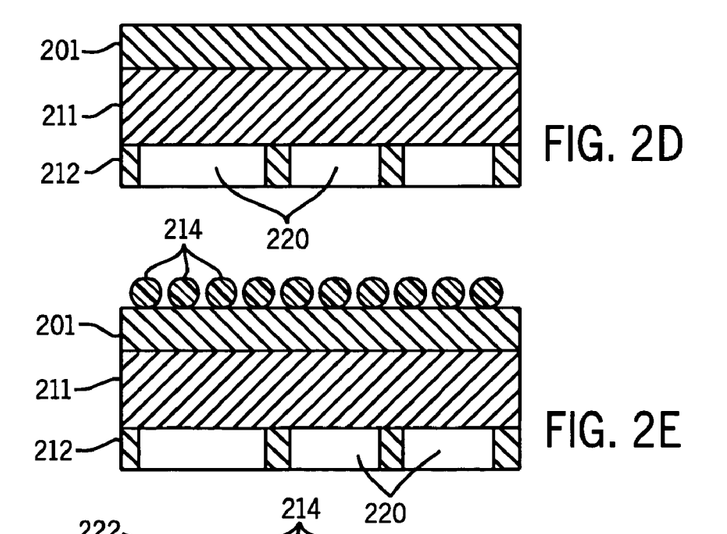

At step 305 in FIG. 3, corresponding to FIG. 2D, openings 220 are formed in the substrate mask material 200 to form the substrate mask 212. The openings 220 may otherwise be known as recesses, wells, cavities, and the like. The openings 220 are formed in the substrate mask material 200 using a variety of methods, such as photo-resist with an etch process, that are well known in the art of semiconductor processing. The openings 220 extend through the substrate mask material 200 to the bottom surface of the substrate 211 so that portions of the bottom surface of the substrate are exposed. The openings 220 formed in the substrate mask 212 define areas on the bottom side of the substrate 211 that are removed later to form the filter supports. The openings 220 may be formed after any step in the method in FIG. 3 or after any sequence in FIGS. 2B–2K that is appropriate or desirable because the formation of the openings is not dependent on another step. However, the openings 220 need to be formed in the substrate mask material before the openings 224 can be formed in the substrate 211 to form the filter supports (see FIG. 2I).

At step 306 in FIG. 3, corresponding to in FIG. 2E, spacers 214 are deposited on the top surface of the filter material. The spacers 214 may be formed of any material that is compatible with the micro machined fabrication process. Preferably, the spacers are formed of polystyrene, but may also be formed of silica, polymeric, carboxylate (COOH) polystyrene, and the like. The spacers 214 may have any shape and size. Preferably, the spacers 214 are spheres having a diameter in the sub-micron range. Alternatively, the spacers 214 may be cubes, ovals, and irregular or random shapes. The spacers 214 may be solid or hollow. The spacers 214 deposited on the filter material preferably each have the same or nearly similar shapes and sizes, but may also have different shapes and sizes. In the preferred embodiment of the present invention, the spacers 214 are spheres having part number P0002100N from Bangs Lab, 9025 Technology Drive, Fishers, Ind. 46038-2886. In the preferred embodiment, the spacers 214 are deposited on the substrate 211 using deposition process such as electrochemical, ultrasonic spray, aerosol, or spin-on, that are well known in the art of semiconductor processing. The spacers 214 are preferably deposited as a single layer of spacers 214 arranged in a side-by-side relationship, but may also be deposited as multiple layers if desired and appropriate. The spacers 214 may be deposited in a random or predetermined pattern, as desired and appropriate. Preferably, the spacers 214 are carried in a liquid during the deposition process, leaving only the spacers 214 when the liquid dries. The spacers 214 naturally adhere to the surface of the filter material 201 made of polysilicon, but may be made to be attracted to the filter material by using the electrophoresis deposition process, described above, which also increases the density of the spacers 214. The spacers 214 may have any diameter or thickness in the range of 0.05–0.5 micrometers, and are preferably 0.2 micrometers thick. As best seen in FIG. 7H, the spacers 214 are used later in the micromachining process to form holes 222 in a filter mask 215 for the anti-microbial filter 105. Generally, the diameter of the spacers 214 corresponds to the diameter of the holes 222 in the filter mask 215 that, in turn, correspond to the holes 218 in the filter membrane 213 of the anti-microbial filter 105. Therefore, special consideration should be given to the size of the spacers 214 because the size of each spacer 214 indirectly relates to the size of the microorganisms that need to be filtered.

Figure 2F:
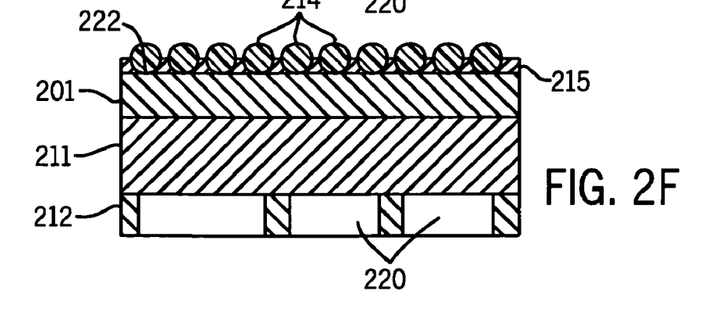

At step 307 in FIG. 3, corresponding to FIG. 2F, filter mask material is deposited around the spacers 214 on the filter material. Preferably, the filter mask material does not completely cover the spacers 214. Further, the filter mask material does not come between the spacers 214 and the filter material 201 where the spacers 214 contact the filter material. In practice, the filter mask material extends about one-half way underneath the spheres because of the curved shape of the spheres against the relatively flat surface of the substrate and the method of deposition used. This relatively imprecise application of the filter mask material is acceptable because the end goal is to have holes 218 in the filter membrane 213 that correspond to the diameter of the spacers 214, as is described later with the remaining steps. The filter mask 215 may be formed of any material that is compatible with the micro machined fabrication process. In the preferred embodiment, the filter mask material is deposited on the filter material 201 using deposition processes such as electrochemical, ultrasonic spray, aerosol, or spin-on, that are well known in the art of semiconductor processing. Preferably, the filter mask 215 is formed of material that does not permit ions to pass through it. Hence, the filter mask 215 may be formed from most refractory metals such as titanium, chrome, tungsten, platinum, nickel, and the like. The filter mask material may have a thickness in the range of 0.05–0.3 micrometers, and is preferably 0.05 micrometers thick. The filter mask material is used later in the micromachining process to form a filter mask 215 for the anti-microbial filter 105.

Figure 2G:
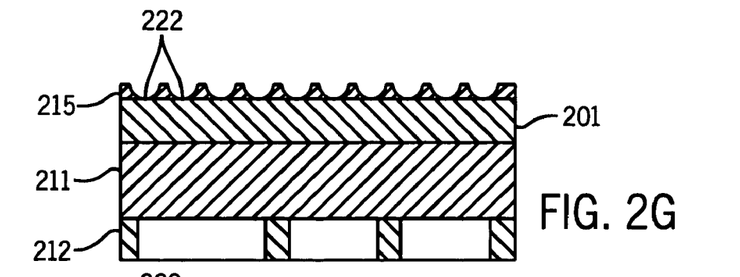

At step 308 in FIG. 3, corresponding to FIG. 2G, the spacers 214 are removed to form holes 222 in the filter mask material to provide the filter mask 215, otherwise called a filter template. The spacers 214 may be removed using any method that is compatible with the micro machined fabrication process. Preferably, the spacers 214 are removed by dissolving the spacers 214 with solutions, such as an acid solution, a base solution or an oxidizing solution. For example, hydrogen peroxide and sulfuric acid each dissolve spacers 214 formed of a polymeric material. Also, for example, acetone can dissolve spacers 214 formed of organics. Alternatively, the spacers 214 may be removed by disintegrating the spacers 214 using processes, including but not limited to ultrasound, ethylenediamine-pyrocatechol-water (EDP), and the like. In practice, since the filter mask material extends about one-half way underneath the spacers 214, as described in step 307, the holes 222 in the filter mask material have a diameter of about one-half the diameter of the spacers 214. In the preferred embodiment of the present invention, it is interesting to note that the process forms the holes 222 in the filter mask 215 by removing an element (i.e., the spacers 214), formed of one material, from the filter mask material, formed of a different material. This preferred method of forming the holes in the filter mask 215 is in contrast to more expensive, time consuming and less precise methods of forming holes in a filter mask, such as by an electron beam, deep ultraviolet light, x-ray, or photolithography.

Figure 2H:
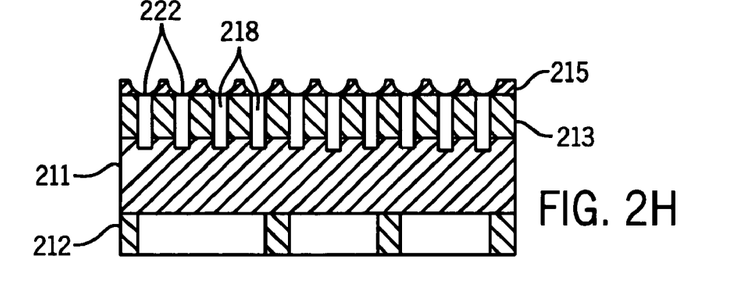

At step 309 in FIG. 3, corresponding to FIG. 2H, holes 218 are formed in the filter material using the filter mask 215 to form the filter membrane 213. The holes 218 extend through the thickness of the filter material. The holes 218 may be formed using any process that is compatible with semiconductor manufacturing processing. In the preferred embodiment of the present invention, a directionally controlled etching process is used to form the holes 218. Preferably, a reactive ion etching (RIE) process is used, but other processes such as ion beam milling may also be used. During the RIE process, ions bombard the filter mask 215. Because of the material of the filter mask 215, as described above in step 307, the ions bounce off the filter mask 215. However, the holes 222 formed in the filter mask 215, as described in step 308, permit the ions to pass through the holes 222 to reach the filter material on the opposite side of the filter mask. The ions react with the filter material to cause the filter material to be selectively removed, as is well known in the art of semiconductor manufacturing processing, to create the holes 218 in the filter material. The speed of formation of the holes 218 and depth of the holes 218 is dependent upon factors such as the intensity and duration of the ion bombardment as well as the filter material. The holes 218 formed in the filter membrane 213 tend to be a little larger than the holes 222 in the filter mask 215 by about one-half the dimension of the spacers 214 due to a bleed through or fringe effect of the ions passing through the holes 222 in the filter mask 215. Since, the holes 222 formed in the filter mask 215, have a diameter about one-half the diameter of the spacers 214, the holes 218 in the filter material having a dimension approximately equal to the dimension of the spacers 214. The holes 218 in the filter material are sized appropriately to effectively filter out unwanted microorganisms.

Figure 2I:
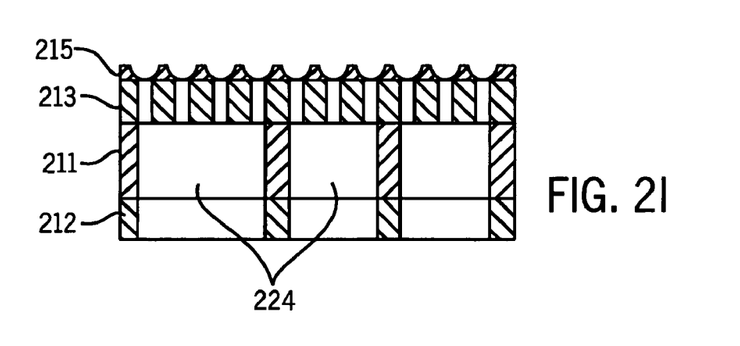

At step 310 in FIG. 3, corresponding to FIG. 2I, holes 224 are formed in the substrate 211 to form the filter supports. The use of filter supports is optional and depends on the structural and material integrity of the filter membrane 213, as well as the construction and material of the MEMS that the filter membrane 213 is integrated with. The holes 224 may be formed using any process that is compatible with semiconductor manufacturing processing, as is well known in the art. The holes 224 extend through the thickness of the substrate 211 and correspond to the openings 220 formed in the substrate mask material 200, as described in step 305. The holes 224 in the substrate 211 expose the holes 218 in the filter membrane 213. By selectively removing the substrate material to form the holes 224, the substrate material that remains forms the filter supports. The number and location of the filter supports may vary as desired and appropriate.

Figure 2J:
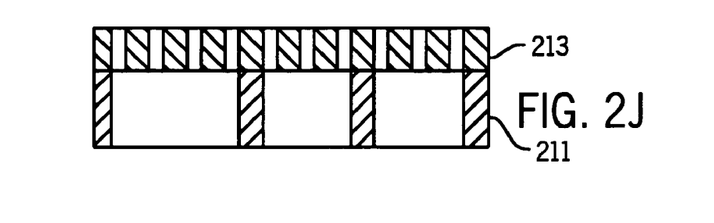

At step 311 in FIG. 3, corresponding to FIG. 2J, the filter mask material and the substrate mask material are removed using methods that are well known in the art of semiconductor manufacturing processing.

Figure 2K:
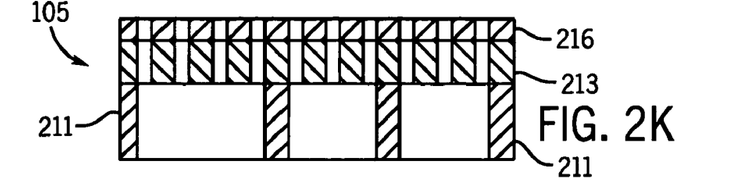

At step 312 in FIG. 3, corresponding to FIG. 2K, a coating 216 is deposited on the side of the filter membrane 213 that is remote from the filter supports. The coating 216, otherwise known as a film, may be deposited using any process that is compatible with semiconductor manufacturing processing, such as electrochemical, ultrasonic spray, aerosol, or spin-on, that are well known in the art of semiconductor processing. Preferably, the coating 216 is formed of a material that does not permit microorganisms to adhere to it and/or kills microorganisms that contact the coating 216. Preferably, the coating 216 is formed of silver. The coating 216 may have a thickness in the range of 0.05 to several microns thick, and is preferably 0.1 micrometers thick. Preferably, the coating 216 is deposited on the downstream side of the filter membrane 213. When fluid flows through the filter membrane 213, the pressure of the fluid typically keeps the microorganisms from moving upstream against the pressure of the fluid to reach the fluid source. However, when or if the pressure of the fluid flow stops, the microorganisms may try to move, by migration or diffusion, upstream through the filter membrane 213. In this case, the coating 216 prevents or inhibits such movement. Depending on the application for the filter membrane 213, the coating 216 is optional.

The steps described above advantageously produce an anti-microbial filter 105 that is small enough to be used in the micro-fluidic system 100. The anti-microbial filter 105 is constructed using micro-machining processes to permit it to be integrated into the micro-fluidic system 100. The anti-microbial filter 105 has precisely defined hole sizes that are cost effective and easy to manufacture. The filter 105 reliably filters out unwanted microorganisms. In the preferred embodiment of the present invention, the anti-microbial filter 105 is used in miniature or micro-sized intravenous or implanted drug delivery systems.

Figure 4:
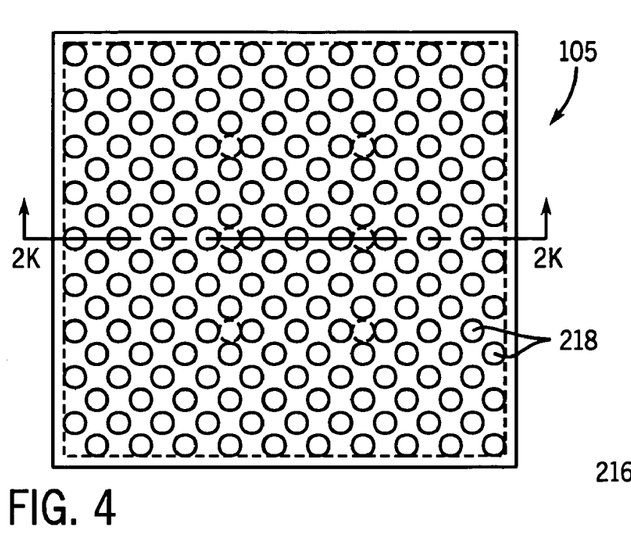
FIG. 4 is a top plan view of the anti-microbial filter of FIG. 1.
Figure 5:
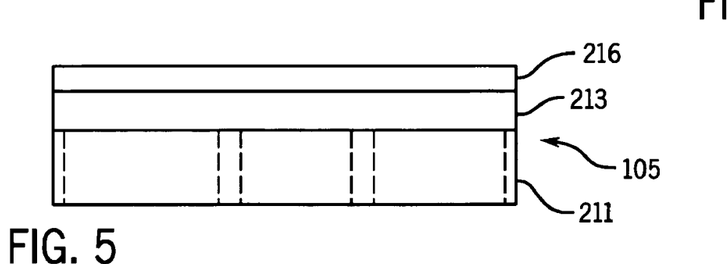
FIG. 5 is a front elevation view of the anti-microbial filter of FIG. 1.
Figure 6:
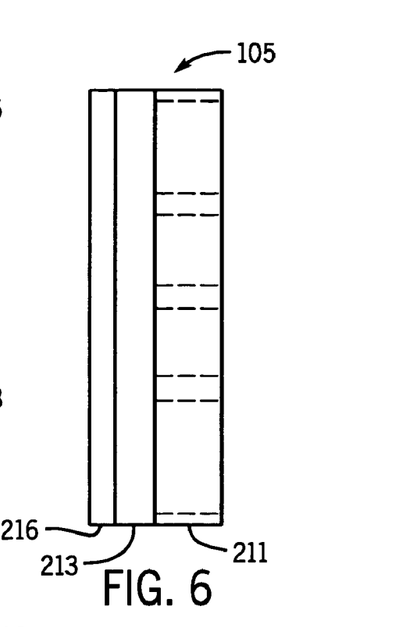
FIG. 6 is a right side elevation view of the anti-microbial filter of FIG. 1.
Figure 7:
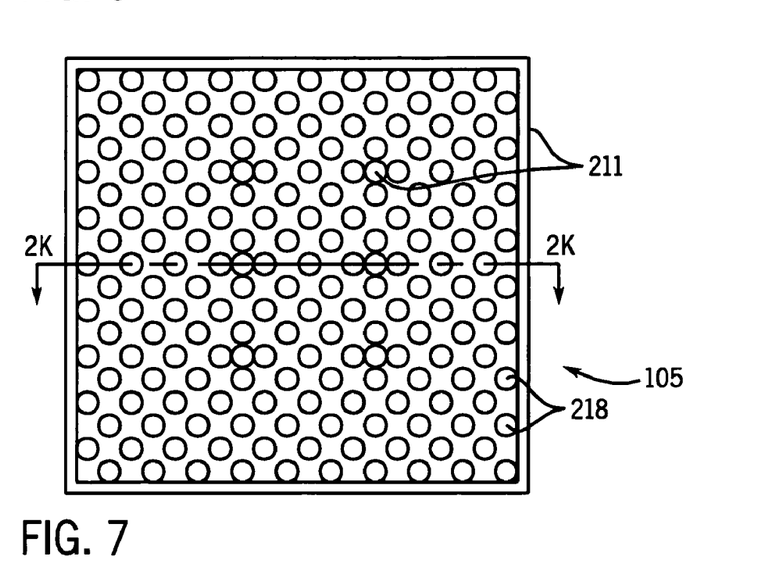
FIG. 7 is a plan view of the bottom of the anti-microbial filter of FIG. 1.

FIGS. 4–7 illustrate the top, front, right and bottom views of the anti-microbial filter 105 respectively. FIGS. 5 and 6 show the coating 216 disposed on the filter membrane 213 that is formed on the substrate 211. FIGS. 4 and 7 show the holes 218 formed in the anti-microbial filter 105. FIG. 7 shows the substrate 211 formed as filter supports comprising a wall along the perimeter of the filter 105 and six posts inside the perimeter of the filter 105. FIG. 4 shows the filter supports with dashed lines because they are hidden in this view.

The size and shape of the anti-microbial filter 105, as viewed in the FIG. 4 and FIG. 7, may vary as desired and appropriate for a particular application. The shape of the anti-microbial filter 105, as viewed in FIGS. 4 and 7, may be square, rectangular, round, oval, a shape having any number of sides, as well as any irregular shape. In the preferred embodiment of the present invention, the size of the anti-microbial filter 105, as viewed in FIGS. 4 and 7, is in the range of tens of microns to several millimeters and is preferably 1 mm×1 mm. In the preferred embodiment of the present invention, the thickness of the anti-microbial filter 105, as viewed in the elevation views FIGS. 5 and 6, is in the range of 0.1 and 50 micrometers and is preferably 3 micrometers.

Figure 8:
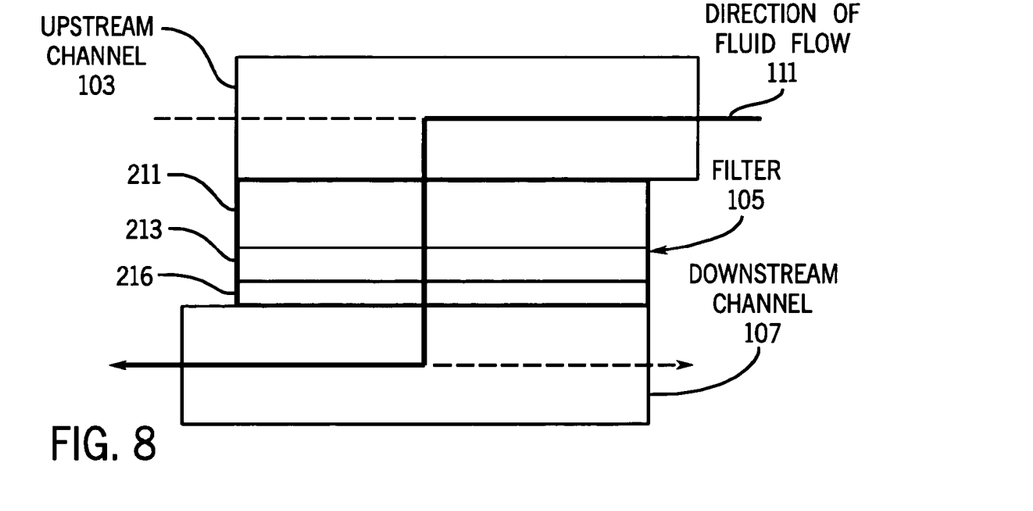
FIG. 8 illustrates an elevation view of a semiconductor construction for the upstream channel, the anti-microbial filter and the downstream channel according to a first embodiment of the present invention.
Figure 9:
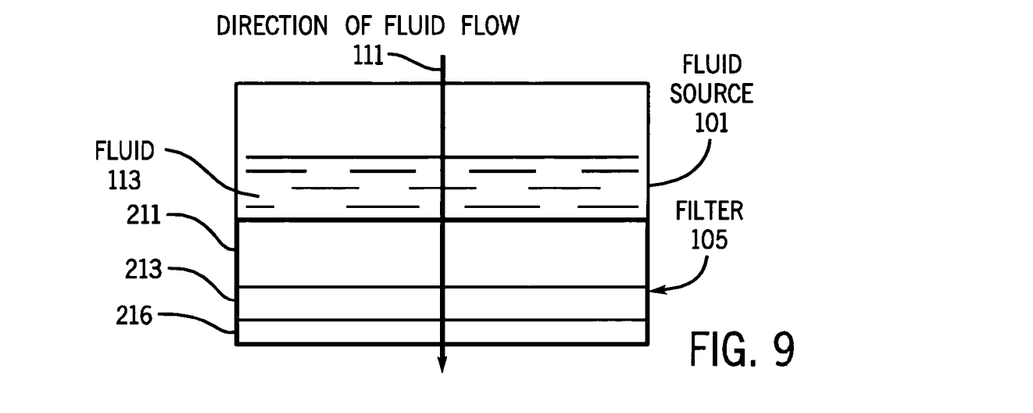
FIG. 9 illustrates an elevation view of a semiconductor construction for the fluid source and the anti-microbial filter according to a second embodiment of the present invention.
Figure 10:
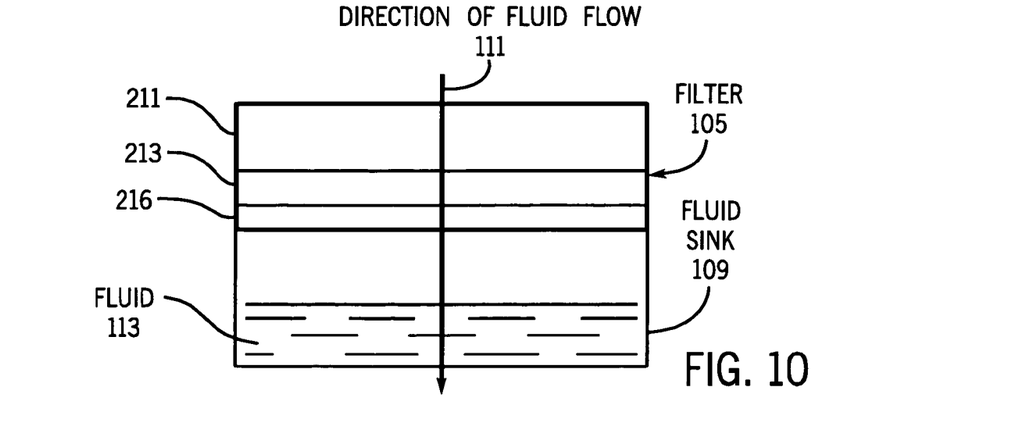
FIG. 10 illustrates an elevation view of a semiconductor construction for the anti-microbial filter and the fluid sink according to a third embodiment of the present invention.

Next, FIGS. 8, 9 and 10 are described together. FIG. 8 illustrates an elevation view of a semiconductor construction for the upstream channel 103, the anti-microbial filter 105 and the downstream channel 107 in accordance with one embodiment of the present invention. FIG. 9 illustrates an elevation view of a semiconductor construction for the fluid source 101 and the anti-microbial filter 105, in accordance with another embodiment of the present invention. FIG. 10 illustrates an elevation view of a semiconductor construction for the anti-microbial filter 105 and the fluid sink 109, in accordance with another embodiment of the present invention.

Generally, in FIGS. 8, 9 and 10, the upstream channel 103, the downstream channel 107, the anti-microbial filter 105, the fluid source 101 and the fluid sink 109 are formed using micro-machining processes and materials compatible with semiconductor construction. Preferably, the semiconductor construction is planar to permit the upstream channel 103, the downstream channel 107, the anti-microbial filter 105, the fluid source 101 and the fluid sink 109 to be assembled in a stacked arrangement using known assembly processes and materials. Any of the individual elements may be integrated with each other, if desired and appropriate for a particular application. The coating 216 on the anti-microbial filter 105 is orientated to be on the downstream side of the anti-microbial filter 105 to prevent microorganisms from moving upstream through the filter 105.

In FIG. 8, the upstream channel 103 and the downstream channel 107 represent a fluid channel, preferably formed in semiconductor material, using micro-machining techniques. Preferably, the fluid flows into the right side of the upstream channel 103, but may alternatively flow into the left side of the upstream channel 103 (as shown by dashed lines) or into both the right and left sides of the upstream channel 103. Likewise, the fluid flows out of the left side of the downstream channel 107, but may alternatively flow out of the right side of the downstream channel 107 (as shown by dashed lines) or out of both the left and right sides of the downstream channel 107. The anti-microbial filter 105 is disposed between the upstream channel 103 and the downstream channel 107. The substrate 211 forming the filter support contacts the upstream channel 103. The coating 216 on the filter membrane 213 contacts the downstream channel 107.

In FIG. 9, the fluid source 101 directly contacts the anti-microbial filter 105, without having the upstream channel 103 disposed between the fluid source 101 and the anti-microbial filter 105. In this case, the substrate 211 forming the filter support contacts the fluid source 101.

In FIG. 10, the fluid sink 109 directly contacts the anti-microbial filter 105, without having the downstream channel 107 disposed between the fluid sink 107 and the anti-microbial filter 105. In this case, the coating 216 contacts the fluid sink 107.

Hence, while the present invention has been described with reference to various illustrative embodiments thereof, the present invention is not intended that the invention be limited to these specific embodiments. Those skilled in the art will recognize that variations, modifications and combinations of the disclosed subject matter can be made without departing from the spirit and scope of the invention as set forth in the appended claims.

What is claimed is:

1. A method for making an anti-microbial filter for a micro-fluidic system, the method comprising the steps of:

providing a substrate;

forming a filter membrane of a filter material on the substrate; and forming a plurality of holes through the filter membrane by providing a filter mask having a plurality of holes therein over the filter membrane by depositing a plurality of spacers on the filter material such that a part of each of the spacers contacts the filter material to define said plurality holes in the filter mask, depositing filter mask material partially around the spacers and on the filter material such that the part of each of the spacers that contacts the surface of the filter material prevents the filter mask material from continuously coming between the spacers and the filter material and thereby defines one of the plurality of holes in the filter mask, removing the plurality of spacers to form the plurality of holes in the filter mask, and forming the plurality of holes in the filter membrane in registration with the plurality of holes in the filter mask; and removing at least a portion of the substrate to expose at least some of the holes in the filter membrane;

wherein, said spacers are sub-micron particles selected from polystyrene, silica or carboxylate polystyrene.

2. The method according to claim 1, wherein the step of forming the filter membrane further comprises the step of:

diffusing filter material into a predetermined depth of the substrate, wherein the predetermined depth of the diffusion of the filter material into the substrate corresponds to a predetermined thickness of the filter membrane.

3. The method according to claim 1, wherein the step of forming the filter membrane further comprises the step of:

depositing the filter membrane on the substrate.

4. The method according to claim 1, wherein the step of removing the plurality of spacers further comprises the step of:

dissolving the plurality of spacers.

5. The method according to claim 1, wherein the step of removing the plurality of spacers further comprises the step of:

disintegrating the plurality of spacers.

6. The method according to claim 1, wherein the step of forming the plurality of holes in the filter membrane comprises the step of:

etching the filter membrane through the holes in the filter mask.

7. The method according to claim 1 comprising the step of:

depositing an anti-microbial coating between the holes on the filter membrane.

8. The method according to claim 7 wherein the anti-microbial coating contains silver.

9. The method according to claim 6, wherein the etching step includes reactive ion etching.

* * * * *